(12) United States Patent
Bond et al.

(10) Patent No.: US 10,556,852 B2
(45) Date of Patent: Feb. 11, 2020

(54) PRODUCTION OF MALEIC ACID, FUMARIC ACID, OR MALEIC ANHYDRIDE FROM LEVULINIC ACID ANALOGS

(71) Applicants: Jesse Quentin Bond, Syracuse, NY (US); Anargyros Chatzidimitriou, Syracuse, NY (US)

(72) Inventors: Jesse Quentin Bond, Syracuse, NY (US); Anargyros Chatzidimitriou, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 16/003,330

(22) Filed: Jun. 8, 2018

(65) Prior Publication Data

US 2018/0354883 A1   Dec. 13, 2018

Related U.S. Application Data

(60) Provisional application No. 62/516,770, filed on Jun. 8, 2017.

(51) Int. Cl.
| | |
|---|---|
| C07C 51/31 | (2006.01) |
| B01J 23/22 | (2006.01) |
| B01J 37/02 | (2006.01) |
| B01J 37/00 | (2006.01) |
| B01J 21/04 | (2006.01) |
| B01J 37/14 | (2006.01) |

(52) U.S. Cl.
CPC ............ *C07C 51/313* (2013.01); *B01J 21/04* (2013.01); *B01J 23/22* (2013.01); *B01J 37/0036* (2013.01); *B01J 37/0201* (2013.01); *B01J 37/14* (2013.01)

(58) Field of Classification Search
None
See application file for complete search history.

(56) References Cited

U.S. PATENT DOCUMENTS

| | | | | |
|---|---|---|---|---|
| 3,492,337 | A * | 1/1970 | La Bar | C07C 67/313 560/156 |
| 2015/0191411 | A1 * | 7/2015 | Bond | C07C 51/245 562/582 |

* cited by examiner

*Primary Examiner* — Sudhakar Katakam
*Assistant Examiner* — Jennifer C Sawyer
(74) *Attorney, Agent, or Firm* — Bond Schoeneck & King, PLLC; David Nocilly

(57) ABSTRACT

A system and method for the conversion of a levulinate ester to maleic anhydride using a reducible oxide catalyst. Levulinic acid oxidation delivers maleic anhydride in good yields without viscosity and stability issues that make continuous production problematic. Due to the fact that levulinate esters are more amenable to processing, the conversion of levulinate esters to maleic anhydride represents an appropriate for the commercial production of maleic anhydride from renewable resources.

8 Claims, 3 Drawing Sheets

PRODUCTION OF MALEIC ACID, FUMARIC ACID, OR MALEIC ANHYDRIDE FROM LEVULINIC ACID ANALOGS

CROSS-REFERENCE TO RELATED APPLICATIONS

The present application claims priority to U.S. Provisional App. No. 62/516,770, filed on Jun. 8, 2017.

STATEMENT REGARDING FEDERALLY SPONSORED RESEARCH OR DEVELOPMENT

This invention was made with government support under Contract No. 1454346 awarded by the National Science Foundation (NSF). The government has certain rights in the invention.

BACKGROUND OF THE INVENTION

1. Field of the Invention

The present invention relates to the production of maleic acid and, more specifically, to process for the production of maleic acid or related compounds, such as fumaric acid, from methyl levulinate or other levulinate esters.

2. Description of the Related Art

Levulinic acid is generally prepared by two methods. First, it can be synthesized by acid hydrolysis of cellulose, glucose, or any other type of 6-carbon sugar or polymer of 6-carbon sugars. Second, it can be prepared by hydrolysis/hydration of furfuryl alcohol. Furfuryl alcohol is a hydrogenated furfural derivative; as such, it is sourced from 5-carbon sugars or polymers of 5-carbon sugars. Often, it is advantageous to synthesize levulinic acid (from its various precursors) in alcohol solvents. In the presence of alcohols, levulinic acid, which is a carboxylic acid, will form its analogous ester by dehydration/esterification with the alcohol. For example, in the presence of ethanol, levulinic acid will form ethyl levulinate.

Levulinate esters offer comparable chemical flexibility to levulinic acid; therefore, they are another interesting type of bio-based platform chemical. Both have been targeted as precursors to various solvents, fuels, commodity, and fine chemicals; however, levulinate esters offer a few processing advantages over levulinic acid. For example, levulinic acid has a high melting point 25° C.) and high viscosity, which can be problematic in continuous operation (as it generally requires either heat tracing or a solvent to ensure fluidity). Furthermore, levulinic acid is thermally unstable, reactive, and has a very low vapor pressure. These characteristics make gas phase processing challenging, which is unfortunate as it can hinder industrial application of some interesting vapor-phase upgrading chemistries. For example, the production of maleic anhydride through the aerobic gas phase oxidation of levulinic acid over a reducible metal oxide was recently demonstrated. Maleic anhydride is the anhydride form of two four-carbon diacids: trans-butenedioic acid (fumaric acid) and cis-butenedioic acid (maleic acid), and it is presently a large-market commodity chemical. While levulinic acid oxidation can deliver maleic anhydride in good yields, the aforementioned practical challenges in levulinic acid handling may limit industrial applicability. Thus, there remains a need in the art for an industrially applicable approach that can deliver maleic anhydride in good yields.

BRIEF SUMMARY OF THE INVENTION

The present invention comprises the oxidation of methyl levulinate, a representative ester of levulinic acid, to form maleic anhydride. More specifically, reducible oxide catalyst was used to facilitate the formation of maleic anhydride through the oxidative cleavage of methyl levulinate. Levulinate esters, such as methyl levulinate, generally have lower melting points, higher vapor pressures, lower viscosity, and better thermal stability, making them more amenable to handling in continuous processes in general and gas phase processes in particular. Levulinate esters are converted to maleic anhydride over reducible oxide catalysts by leveraging their chemical similarity to levulinic acid. Because levulinate esters are more amenable to processing, the present invention represents a practical advance in the production of maleic anhydride from renewable resources. Finally, because levulinate esters can interconvert with levulinic acid and angelicalactones, this process can also be applied for the production of maleic anhydride, maleic acid, or fumaric acid from angelicalactones.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
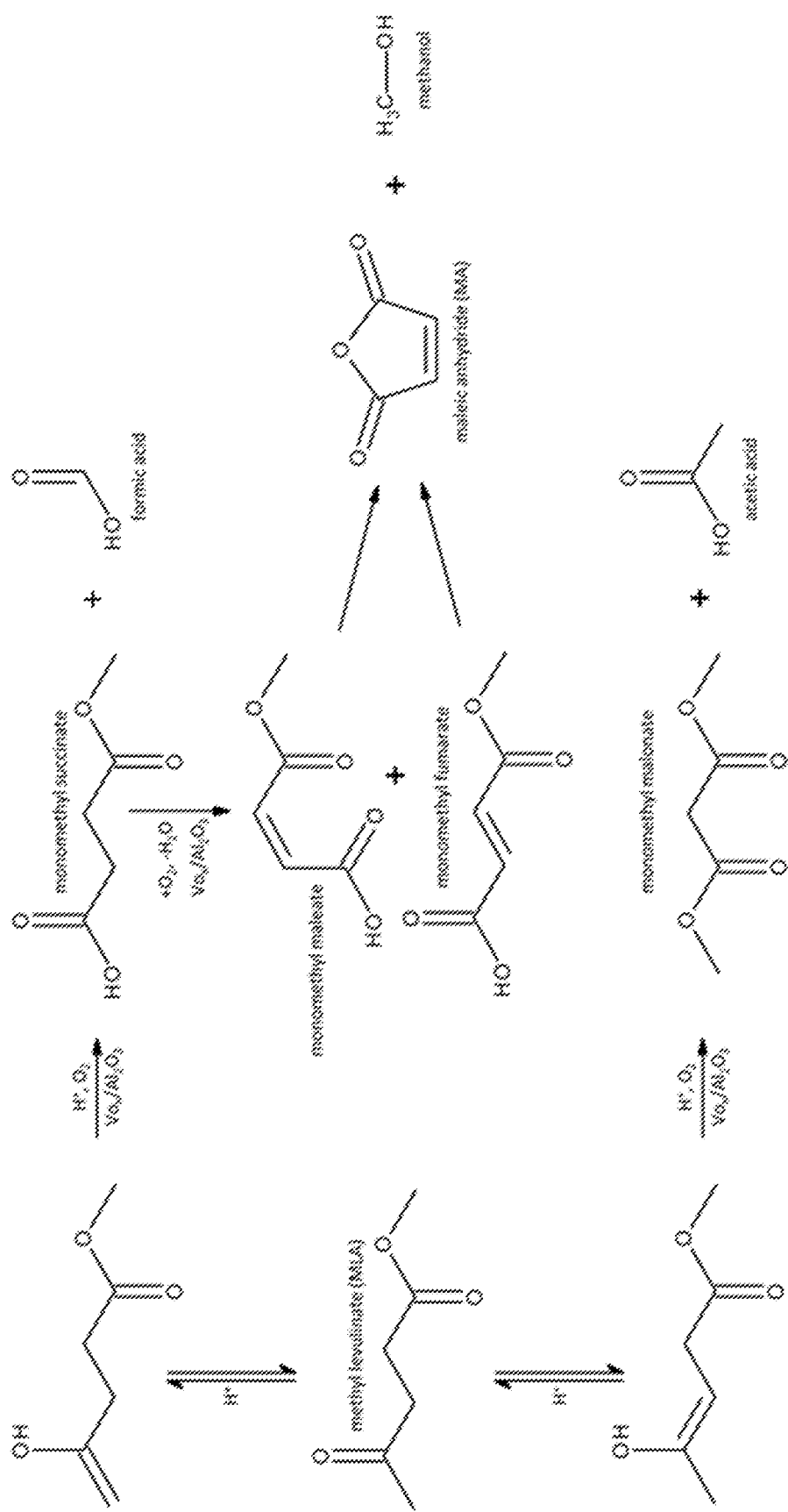
FIG. 1 is a schematic of a pathway for the formation of maleic anhydride through the oxidative cleavage of methyl levulinate.
Figure 2:
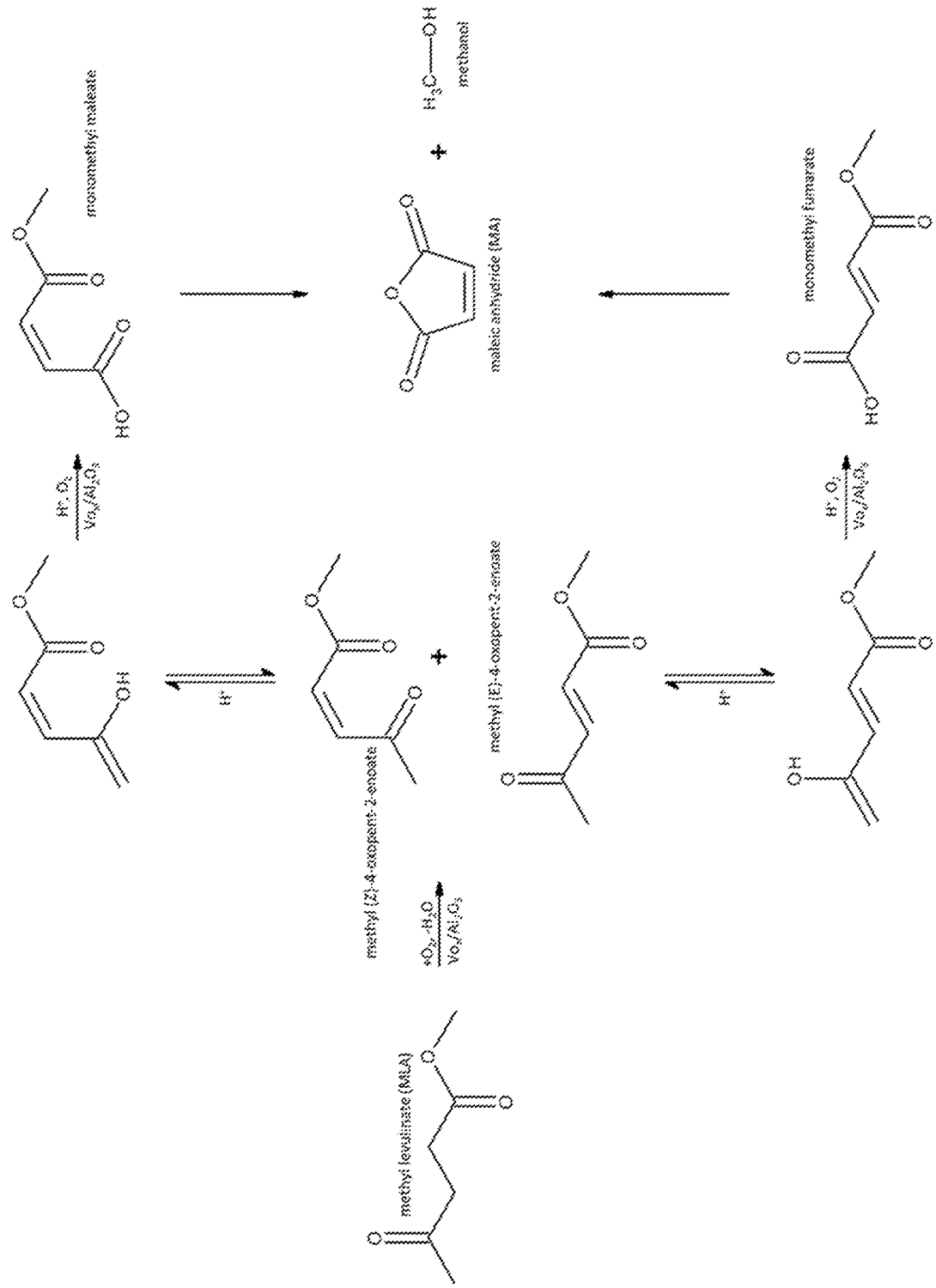
FIG. 2 is a schematic of an alternative pathway for the formation of maleic anhydride through the oxidative cleavage of methyl levulinate.
Figure 3:
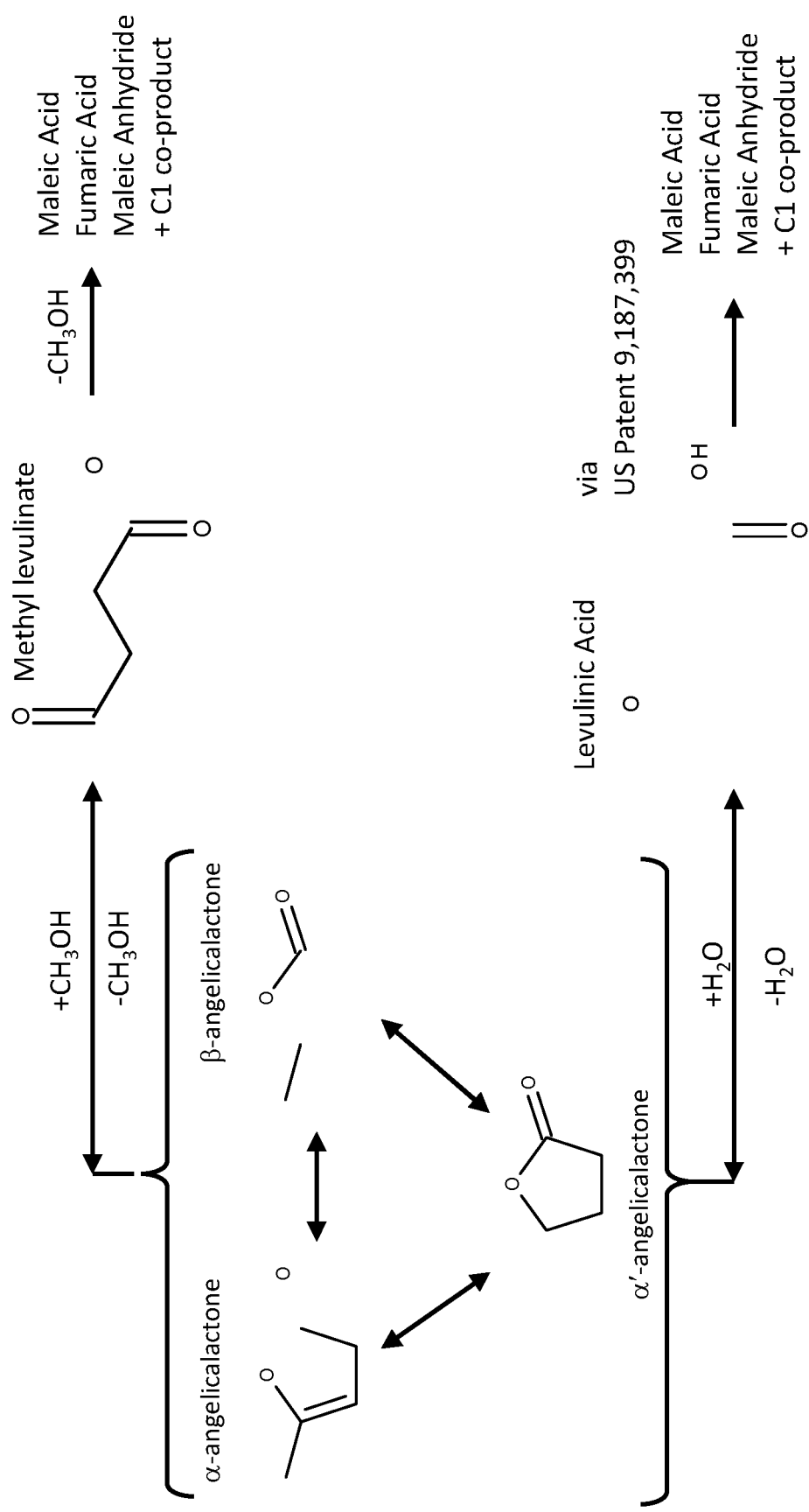
FIG. 3 is a schematic illustrating the interconversion of levulinate esters and levulinic acid with angelicalactones.

Referring to the figures, wherein like numerals refer to like parts throughout, there is seen in FIGS. 1 and 2, two distinct pathways for the formation of maleic anhydride (MA) through the oxidative cleavage of methyl levulinate (ML). As discussed below, preliminary data establishes that the oxidation of methyl levulinate, a representative ester of levulinic acid, may be used to form maleic anhydride. FIG. 3 illustrates the interconversion of levulinic acid and levulinate esters with all angelicalactone isomers. Because angelicalactones can interconvert with either levulinic acid and levulinate esters under reaction conditions, they can also be converted into maleic anhydride or its diacid analogs using the approach described here or, for example, in U.S. Pat. No. 9,187,399, incorporated by reference herein in its entirety. Thus, because levulinic acid and levulinate esters will reversibly form angelicalactones under the reaction conditions reported here, the present invention may be extended to produce maleic anhydride, maleic acid, or fumaric acid from various angelicalactones.

EXAMPLE

The reducible oxide catalyst used in this study was a vanadium oxide ($VO_x$) supported at monolayer loading on γ-$Al_2O_3$. The catalyst was prepared by incipient wetness impregnation of vanadium oxalate onto γ-$Al_2O_3$. A solution of oxalic acid and ammonium metavanadate at a molar ratio of 2:1 was used to wet the surface of the alumina. The resulting powder was crushed and sieved to achieve uniform particle size and was activated by a stream of air (Airgas Ultra Zero) for 4 hours at 723 K.

The $VO_x/Al_2O_3$ sample was then loaded into a catalytic packed bed reactor into which methyl levulinate and molecular oxygen was introduced in a helium diluent. ML was delivered into the system as a liquid using a Cole Parmer syringe pump (Model 100), while $O_2$ (Airgas UHP) and He (Airgas UHP) were supplied by two Brooks 5850S mass flow controllers. ML, $O_2$ and He were preheated to 403 K and mixed in a ½" vessel field filled with quartz chips, which served to vaporize the ML. The gaseous mixture of ML, $O_2$, and He was then preheated to reaction temperature and fed to the reactor. The effluent was kept at 473 K to avoid any product condensation and was guided to an HP 5890 gas chromatograph complete with a pair of heated gas sampling valves. Carbon oxide quantification was achieved through a TCD detector at the end of a Restek Shincarbon ST micropacked column, while the remaining product stream was quantified with a Restek Rtx-1701 column connected to an FID detector. All temperatures were monitored with type K Omega thermocouples, and the system temperature was controlled using series 16A Controllers (Love Controls).

FIGS. 1 and 2 illustrate, based on product stream composition, what is believed to be two distinct pathways for the formation of MA through the oxidative cleavage of ML. In the reaction network of FIG. 1, ML forms two possible enols. Oxidative cleavage of the internal enol yields monomethyl malonate and acetic acid. Oxidative cleavage of the terminal enol yields monomethyl succinate and formic acid. The monomethyl succinate forms monomethyl maleate and/or monomethyl fumarate, through an oxidative dehydrogenation (ODH) step. Either of the above can form MA with the simultaneous release of methanol.

In the pathway of FIG. 2, ML undergoes ODH to yield methyl (Z)-4-oxopent-2-enoate and/or methyl (E)-4-oxopent-2-enoate. Here, the transformation to the internal enol (forming a cumulated diene) will be much less stable than that of the terminal one (forming a conjugated diene). Methyl maleate forms upon oxidative cleavage and releases methanol to give the anhydride. Based on detailed GC-MS analysis of reaction products, there is strong evidence to support that both pathways (FIG. 1 and FIG. 2) are plausible. Should the ODH step become more facile than either enolization step, then the selectivity towards MA should be further enhanced. In the presence of methanol and water, carboxylic groups in both schemes can undergo esterification, while esters can hydrolyze to their respective carboxylic acids and we expect the presence of all those species.

Using the aforementioned configuration and equipment, the data collected is presented in Table 1 below.

TABLE 1

Reaction conditions and results

| Catalyst | Feed rate (umol/min) | Space Velocity (min$^{-1}$) | ML partial pressure (bar) | $O_2$ partial pressure (bar) | Temperature (K) | Conversion (%) |
|---|---|---|---|---|---|---|
| $VO_x$/γ-$Al_2O_3$ | 37.6 | 0.27 | 0.019 | 0.205 | 588 | 100 |

| Production rates (umol/min) | | | | MA yield (% of theoretical) | Internal cleavage selectivity (%) | Terminal cleavage selectivity (%) |
|---|---|---|---|---|---|---|
| MA | Methanol | Acetic acid | $CO_x$ | | | |
| 18.9 | 1.0 | 10.1 | 134.2 | 51 | 35 | 65 |

Preliminary data thus suggests good MA yields can be achieved from the oxidative cleavage of ML. Further optimization of catalysts and operating conditions is likely to increase MA yield. Thus, a whole family of compounds including levulinic acid, levulinic acid esters and angelicalactones can undergo oxidative cleavage, either separately or combined, at the same conditions and over the same metal oxide catalyst, to yield maleic acid, fumaric acid and MA.

What is claimed is:

1. A method of producing maleic anhydride, comprising the step of oxidizing a quantity of methyl levulinate without forming levulinic acid to form maleic anhydride.

2. The method of claim 1, wherein the step of oxidizing the quantity of methyl levulinate to form maleic anhydride comprises the use of a reducible oxide catalyst.

3. The method of claim 2, wherein the reducible oxide catalyst is vanadium oxide ($VO_x$) supported at monolayer loading on γ-$Al_2O_3$ ($VO_x$/γ-$Al_2O_3$).

4. The method of claim 3, further comprising the step of producing the reducible oxide catalyst by incipient wetness impregnation of vanadium oxalate onto γ-$Al_2O_3$ to form a powder.

5. The method of claim 4, wherein the step of producing the reducible oxide catalyst further comprises the step of crushing the powder to achieve a uniform particle size.

6. The method of claim 5, further comprising the step of activating the powder by applying a stream of air for four hours at 723 K.

7. The method of claim 6, wherein the step of oxidizing a quantity of methyl levulinate to form maleic anhydride comprises introducing the quantity of methyl levulinate and a quantity of oxygen in a diluent of helium into a reactor having a packed bed of the reducible oxide catalyst.

8. The method of claim 7, wherein the quantity of methyl levulinate, the quantity of molecular oxygen, and the helium diluent were preheated to 403 K in a vessel field filled with quartz chips.

* * * * *